United States Patent [19]

Bostick et al.

[11] Patent Number: 5,162,049

[45] Date of Patent: Nov. 10, 1992

[54] MIDDLE DISTILLATE FUELS AND ADDITIVES THEREFOR

[75] Inventors: John G. Bostick, Smithton, Ill.; Lawrence J. Cunningham, Kirkwood, Mo.

[73] Assignee: Ethyl Petroleum Additives, Richmond, Va.

[21] Appl. No.: 756,576

[22] Filed: Sep. 9, 1991

[51] Int. Cl.$^5$ .................. C10L 1/22; C10L 1/10; C10M 133/42
[52] U.S. Cl. .................. 44/336; 44/335; 44/420; 252/50
[58] Field of Search .......... 44/336, 335, 384, 420, 44/426; 232/50

[56] References Cited

U.S. PATENT DOCUMENTS

| 2,675,382 | 4/1954 | Melamed | 544/83 |
|---|---|---|---|
| 2,714,057 | 7/1955 | Chenicek | 44/336 |
| 2,852,354 | 9/1958 | Schubert et al. | 44/336 |
| 2,867,515 | 1/1959 | Andress | 44/336 |
| 2,889,277 | 6/1959 | Hughes | 252/8.555 |
| 2,983,099 | 5/1961 | Doumani et al. | 44/384 |
| 3,199,964 | 8/1965 | Arkell et al. | 44/420 |
| 3,424,683 | 1/1969 | Dazzi et al. | 252/50 |
| 3,591,598 | 7/1971 | Traise et al. | 564/304 |
| 3,694,440 | 9/1972 | Knell et al. | 252/50 |
| 3,718,445 | 2/1973 | Troffkin et al. | 44/270 |
| 3,763,094 | 10/1973 | Knell et al. | 524/100 |
| 3,884,917 | 5/1975 | Ibbotson | 544/180 |
| 3,915,970 | 10/1975 | Limaye et al. | 544/215 |
| 4,003,718 | 1/1977 | Gattuso | 44/334 |
| 4,003,719 | 1/1977 | McCoy et al. | 44/420 |
| 4,116,875 | 9/1978 | Nnadi et al. | 44/336 |
| 4,514,286 | 4/1985 | Wang et al. | 44/335 |
| 4,585,462 | 4/1986 | Kitchen, III | 44/336 |

FOREIGN PATENT DOCUMENTS 2414242 10/1975 Fed. Rep. of Germany .
1392171 4/1975 United Kingdom .

OTHER PUBLICATIONS t-alkyl Primary Amines, Rohm & Haas Company, pp. 1-2 Sep. 1963.

Primary Examiner—Prince Willis, Jr.
Assistant Examiner—James M. Silbermann
Attorney, Agent, or Firm—David E. LaRose

[57] ABSTRACT

This invention relates to stabilizer additives for hydrocarbonaceous fuels comprising at least one or a mixture of hexahydrotriazine compounds and at least one or a mixture of imine compounds.

27 Claims, No Drawings

MIDDLE DISTILLATE FUELS AND ADDITIVES THEREFOR

TECHNICAL FIELD

This invention relates to compositions containing a major amount of fuel or lubricant and a minor amount of additive sufficient to stabilize the fuel or lubricant, the additive comprising (i) a hexahydrotriazine and (ii) an imine compound.

THE INVENTION

Accordingly this invention provides an additive composition suitable for use in lubricants and fuels comprising one or a mixture of substituted hexahydrotriazines of the formula

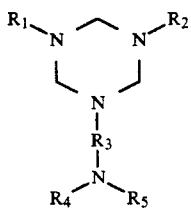

wherein $R_1$ is a hydrocarbyl group, preferably a cycloalkyl group, most preferably a cyclohexyl group; $R_2$ is either a hydrocarbyl group, preferably a cycloalkyl group, most preferably a cyclohexyl group or a dihydrocarbylaminoalkyl group, preferably a dialkylaminoalkyl group, most preferably a dimethylaminopropyl group; $R_3$ is an alkylene group having up to 12 carbon atoms, preferably an alkylene group having 2 to 10 carbon atoms, most preferably a trimethylene (propylene) group; and $R_4$ and $R_5$ are hydrocarbyl groups having from 1 to 20 carbon atoms, preferably alkyl groups, most preferably methyl groups; and one or a mixture of imine compounds of the formula $$R_6-N=R_7$$

wherein $R_6$ is an tertiary substantially aliphatic group having from 4 to 500 carbon atoms, for example, tertiary butyl, t-decyl-t-eicosyl, t-pentacontyl, etc. and $R_7$ is an alkyl group having 1-6 carbon atoms. Preferably, $R_6$ has 4 to 20 carbon atoms; for example t-butyl, t-pentyl, t-hexyl, t-heptyl, t-oxtyl, t-nonyl, t-decyl, t-dodecyl, t-tetradecyl, t-hexadecyl, t-octadecyl, t-eicosyl, etc. most preferably tertiary alkyl groups having from 12 to 14 carbon atoms. Preferably $R_7$ is a methyl group, and most preferably, the imine is a methyl-imine of Primene 81-R (Rohm & Haas Chemical Company).

The compositions of this invention are useful stabilizers for oleaginous liquids such as natural and synthetic oils of lubricating viscosity, and liquid petroleum-based fuels such as gasoline, and fuels heavier than gasoline such as middle distillate fuels and fuel oils (e.g., diesel fuels, burner fuels, jet fuels, heating gas oils, cycle gas oils, vacuum gas oils, etc.), and residual fuels. This invention thus provides in one of its embodiments, a liquid hydrocarbonaceous fluid containing a minor stabilizinq amount of (i) one or a mixture of hexahydrotriazine compounds and (ii) one or a mixture of imine compounds of this invention. Such compositions may also include other known conventional additives of the types useful in the type of hydrocarbonaceous liquid being used.

This invention also provides a concentrate for use in oleaginous liquids which comprise from about 0 to 100 percent by weight of one or more of the substituted hexahydrotriazines of this invention, preferably from about 5 to about 95 percent by weight from about 100 to about 0 percent by weight of one or more of the imines of this invention, preferably from about 95 to 5 percent by weight and from about 0 to about 60 percent by weight of a solvent or diluent which is miscible with and/or capable of dissolving in the oleaginous liquid in which the concentrate is to be used.

Preferred compositions of this invention comprise liquid hydrocarbonaceous fuels heavier than gasoline containing a minor stabilizing amount of at least one or a mixture of hexahydrotriazine compounds and at least one or a mixture of imine compounds as disclosed herein. Such fuels include residual fuels, kerosene, jet fuels, heating oils, diesel fuels, light gas oil, heavy gas oil, light cycle gas oils, heavy cycle gas oils, vacuum gas oils, and the like. Most preferably the fuel is a middle distillate fuel such as a diesel fuel, kerosene, jet fuels, house heating oil or the like. Such middle distillates usually boil in the range of 350° to 700° F. and have cloud points typically in the range of −78° F. to about 45° F. The hydrocarbon stock can comprise straight run and thermally and/or catalytically cracked distillates. Oxygenated blending components of suitable distillation characteristic Mw such as heavy ethers, alcohols and/or esters boiling within the boiling range of the middle distillate itself can be present in minor amounts in the fuel composition(s).

Particularly desirable additive combinations for use in such hydrocarbonaceous middle distillate fuels include the following:

(a) a combination comprising (i) at least one hexahydrotriazine of this invention, (ii) at least one imine, and (iii) at least one metal deactivator, preferably an $N,N^1$-disalicylidene-1,2-alkane diamine such as $N,N^1$-disalicylidene-1,2-ethane diamine, $N,N^1$-disalicylidene-1,2-butane diamine, $N,N^1$-disalicylidene-1,2-cyclohexane diamine, etc., and most preferably $N,N^1$-disalicylidene-1,2-propane diamine;

(b) the combination of a) above further including (i) at least one N-(2,6-dialkyl-4-hydroxybenzyl) hexahydropyrimidine or (ii) at least one N,N-bis(2,6-dialkyl-4-hydroxybenzyl)hexahydropyrimidine, or (iii) a mixture of (i) and (ii), wherein the alkyl groups contain up to about 18 carbon atoms and preferably include at least one tertiary alkyl group, and most preferably are all tertiary alkyl groups, especially tertiary butyl groups. The synthesis of such compounds involves reacting a 2,6-dialkylphenol, formaldehyde (or a formaldehyde source such as formalin, etc.) and 1,3-propanediamine in molar ratios of about 1 to 2 moles of dialkylphenol and about 2 to 3 moles of formaldehyde per mole of 1,3-proponediamine at a temperature in the range of 60° to 100° C., such as in refluxing isopropanol.

The hexahydrotriazine compounds of this invention can be prepared by reacting in appropriate proportions at least one primary monoamine (preferably a cycloalkylamine, most preferably cyclohexylamine), formaldehyde or a formaldehyde source (e.g., paraformaldehyde), and an N,N-dihydrocarbyl alkylene diamine (preferably an N,N-dialkyl alkylene diamine, most preferably N,N-dimethyl-1,3-propane diamine).

Illustrative primary monoamines for use in the process include $C_1$ to $C_{100}$, preferably $C_2$ to $C_{24}$, most preferably $C_4$ to $C_{18}$ alkyl or alkenyl amines in which the alkyl or alkenyl group may be straight chain or branched, but not of tertiary configuration; $C_4$ to $C_{40}$, preferably $C_5$ to $C_{18}$, most preferably $C_6$ to $C_{10}$ cycloalkyl or cycloalkenyl amines; $C_6$ to $C_{40}$, preferably $C_6$ to $C_{18}$, most preferably $C_6$ to $C_{14}$ aryl amines; or mixtures thereof. The principal requirement for this reactant is that amino group should not be sufficiently sterically hindered as to prevent the cyclization-condensation reaction from occurring.

Typical diamines for use in the process are those having the formula $H_2N-R_3-N(R_4)(R_5)$ wherein $R_3$, $R_4$ and $R_5$ are as described above. $R_3$ may be an unsubstituted straight chain alkylene group or it may contain one or more side chains. $R_4$ and $R_5$ can be alkyl, alkenyl, cycloalkyl, aralkyl, aryl, alkaryl, or like hydrocarbyl groups containing up to about 100 carbon atoms, preferably up to about 24 carbon atoms, more preferably 1 to 10 carbons atoms, and most preferably are methyl groups. Individual diamines of this type are usually used, but mixtures of two or more such diamines can be used, if desired.

By varying the proportions of the reactants, the composition of the hexahydrotriazine product can be varied. For example, reaction among 2 moles of monoamine and 3 moles of formaldehyde per mole of the diamine yields a product enriched in product of the above formula in which $R_1$ and $R_2$ are both hydrocarbyl groups corresponding to the hydrocarbyl group of the monoamine. On the other hand, when 2 moles of the diamine and 3 moles of formaldehyde are reacted per mole of the monoamine, the product is enriched in hexahydrotriazine of the above formula where $R_1$ is a hydrocarbyl group corresponding to the hydrocarbyl group of the monoamine, and $R_2$ corresponds to $-R-3-N(R_4)(R_5)$. Proportions intermediate to those presented above give rise to mixtures of varying proportions of both such products. Thus in the process of this invention the reactants are generally employed in mole ratios of from about 0.5 to about 2.5 moles of the monoamine(s) and from about 2.5 to about 0.5 moles of the diamine(s) per each 3 moles of HCHO entering into the reaction. Normally an excess of formaldehyde or formaldehyde-producing reactant is employed Reaction temperatures in the range of from about 0° to 30° C. are usually employed, although departures may be made from these ranges whenever deemed necessary or advisable. All that is required is to maintain the reactants at a temperature at which reaction proceeds at a suitable rate and without causing decomposition of the desired product or product mixture.

The reaction may be conducted in bulk or in a suitable inert liquid reaction medium such as a paraffinic or cycloparaffinic or aromatic hydrocarbon solvent, an ether solvent, a halogenated hydrocarbon solvent, or the like.

Usually the formaldehyde reactant is charged to the reaction vessel either concurrently with or subsequent to the charging of the amine reactants. Water formed in the reaction is removed from the reaction mixture either essentially as soon as the water is formed, or after completion of the reaction.

To prepare the imine compounds of this invention, at least one primary monoamine is reacted in appropriate proportions with at least one formaldehyde or a formaldehyde source (e.g., paraformaldehyde, trioxane, formalin, trioxymethylene, etc.), at a temperature and for a period of time sufficient to form the imine compound means for preparing the imine products of this invention are well known in the art (see for example, U.S. Pat. Nos. 3,320,166, 3,272,852, and 4,202,784 incorporated herein by reference as if fully set forth).

In somewhat greater detail tertiary carbinamines(imines) can be prepared by the well-known condensation of about equimolar amounts of a tertiary alkyl primary amine and formaldehyde. The formaldehyde is generally added to the amine at a rate that the temperature does not exceed the decomposition temperature of the tertiary carbinamine in the presence of an aqueous phase. The product of the foregoing reaction of amine and formaldehyde source is an imine and water. The aqueous phase is separated from the organic phase subsequent to the imine formation reaction by heating the organic phase to a temperature sufficient to separate the organic phase from the aqueous phase by distillation, and the organic phase containing the imine product is recovered.

The following Examples 1-10, in which parts and percentages are by weight, illustrate the process of this invention for preparing the hexahydrotriazines and the hexahydrotriazine products formed thereby.

EXAMPLE 1

To a reaction vessel equipped with cooling and heating means and a condenser is charged 89.2 parts of 37% formaldehyde. A preformed mixture of 66.1 parts of cyclohexylamine and 34.0 parts of N,N-dimethyl-1,3-propane diamine is then added to the reaction vessel over a period of 30 minutes while maintaining the temperature below 30° C. After this, the mixture is heated to distill off the water and excess formaldehyde. The product contains as the principal component 1,3-dicyclohexyl-5-(N,N-dimethyl-3'-aminopropyl)hexahydrotriazine.

EXAMPLE 2

The procedure of Example 1 is repeated except that 33.0 parts of cyclohexylamine and 68 parts of N,N-dimethyl-1,3-propane diamine are employed. The principal product is 1-cyclohexylamine,-3,5-di-(N,N-dimethyl-3'-aminopropyl)hexahydrotriazine.

EXAMPLE 3

To a reactor equipped as in Example 1 are added 264.2 parts of cyclohexylamine, 136 parts of N,N-dimethyl-1,3-propane diamine and 175 parts of toluene. To this mixture is added 327 parts of 37% aqueous formaldehyde solution over a period of 20 minutes while keeping the temperature between 20° and 34° C. Then the mixture is heated to remove the water in the form of a toluene-water azeotrope. During this separation procedure additional toluene is periodically added as required. Initially the temperatures are kept at about 58°-65° C. Thereafter a vacuum is gradually applied while slowly increasing the temperature until the temperature reaches 94° C. at 63mm Hg pressure. At this point the separation is discontinued. The residual product is predominantly 1,3-dicyclohexyl-5-(N,N-dimethyl-3-aminopropyl)-hexahydrotriazine.

EXAMPLE 4

The procedure of Example 3 is repeated using an equivalent quantity of lauryl amine in place of cyclohexylamine. The principal product is 1,3-dilauryl-5-(N,N-dimethyl-3'-diaminopropyl)hexahydrotriazine.

EXAMPLE 5

A product composed predominantly of 1,3-dioleyl-5-(N,N-diethyl-3'-aminopropyl)hexahydrotriazine is formed by reacting 2 moles of oleylamine and 1 mole of N,N-diethyl-1,3-propane diamine with 3 moles of formaldehyde while controlling the temperatures to between 20° and 30° C.

EXAMPLE 6

The procedure of Example 5 is repeated using 1.5 moles of each of the amine reactants. The product includes both 1,3-dioleyl-5-(N,N-diethyl-3'-aminopropyl)hexahydrotriazine and 1-oleyl-3,5-di-(N,N-diethyl-3'-aminopropyl)hexahydrotriazine.

EXAMPLE 7

Reaction at 20° to 30° C. among 2 moles of aniline, 1 mole of N,N-dibutyl-1,3-propane diamine and 3 moles of formaldehyde yields a product composed mainly of 1,3-diphenyl-5-(N,N-dibutyl-3'-aminopropyl) hexahydrotriazine.

EXAMPLE 8

Repetition of Example 7 using 2 moles of benzyl amine in place of the aniline forms a product composed mainly of 1,3-dibenzyl-5-(N,N-dibutyl-3'-aminopropyl)-hexahydrotriazine.

EXAMPLE 9

Example 7 is repeated using 2 moles of 2-phenylethyl amine in lieu of 2 moles of aniline whereby a product composed chiefly of 1,3-di-(phenethyl)-5-(N,N-dibutyl-3'-aminopropyl)hexahydrotriazine is formed.

EXAMPLE 10

Example 3 is repeated except that an equivalent amount of decyloxypropyl amine replaces the cyclohexylamine. The product contains 1,3-di-(decyloxypropyl)-5-(N,N-dimethyl-3'-aminopropyl)hexahydrotriazine.

Other hexahydrotriazine compounds of this invention include, for example, the following: 1,3-diethyl-5-(N,N-dimethyl-3'-aminopropyl)hexahydrotriazine, 1,3-diisopropyl-5-(N,N-dimethyl-3'-aminopropyl)hexahydrotriazine, 1,3-dibutyl-5-(N,N-dimethyl-3'-aminopropyl)-hexahydrotriazine, 1,3-di-2-ethylhexyl-5-(N,N-dimethyl-3'-aminopropyl)-hexahydrotriazine, 1,3-di-tetradecyl-5-(N,N-dimethyl-3'-aminopropyl)propyl)hexahydrotriazine, 1-decyl-3-octyl-5-(N,N-dimethyl-3'-aminopropyl)hexahydrotriazine, 1,3-diallyl-5-(N,N-dimethyl-3'-aminopropyl)hexahydrotriazine, 1,3-di-(4-methylcyclohexyl)-5-(N,N-dimethyl-3'-aminopropyl)hexahydrotriazine, 1-cyclohexyl-3-phenyl-5-(N,N-dimethyl-3'-aminopropyl)hexahydrotriazine, 1,3-di(polypropenyl)-5-(N,N-dimethyl-3'-aminopropyl)hexahydrotriazine, 1,3-dibenzyl-5-(N,N-dimethyl-3'-aminopropyl)hexahydrotriazine, 1,3-diphenyl-5-(N,N-dimethyl-3'-aminopropyl)hexahydrotriazine, 1,3-di-m-tolyl-5-(N,N-dimethyl-3'-aminopropyl)hexahydrotriazine, 1,3-dipropyl-5-(N,N-dibutyl-3'-aminopropyl)hexahydrotriazine, 1,3-diphenyl-5-(N,N-dioctyl-4'-aminobutyl)hexahydrotriazine, 1,3-di(polybutenyl)-5-(N,N-dimethyl-3'-aminopropyl)hexahydrotriazine, and the like.

The following Example 11 illustrates a process for the preparation of imine compounds of this invention.

EXAMPLE 11

Primene 81-R (191 grams, 1 mole) was added to a 500 mL round bottom flask. Formalin, 37 wt. % formaldehyde, (89.2 grams, 1.1 moles) was added to the flask with stirring over a ½ hour period. During the formalin addition, the reactants were maintained at a temperature of less than 30° C. by cooling the reaction flask. Subsequent to the addition of the formalin, the temperature of the reaction flask was raised to 100° C. and water was distilled from the reaction mass. Remaining in the flask was 201 grams of a methyl-imine of Primene 81-R representing about a 99% yield based on theoretical.

ASTM D-4625 Storage Stability Test

The color of freshly filtered middle distillate fuel (400 mL) is determined utilizing the ASTM D-1500 method and then the fuel is stored in a suitable container in a darkened area at 43° C. for 13 weeks. After the storage period the color of the fuel is again determined using ASTM D-1500. The deposits are obtained by filtering the fuel and by combining any deposits on the filter media with any deposit that adhered to the walls of the fuel container. The deposits are reported as mg/100 mL of sample.

Accelerated Storage Stability Test (F21-61)

Freshly filtered middle distillate fuel (50 mL) is heated at 149° C. for about 90 minutes. The sample is allowed to cool to room temperature in the dark and the color is determined using the ASTM D-1500 method. The sample is then filtered using a 4.25 cm Whatman #1 filter paper and the filtrate discarded. The filter paper is washed clean of fuel and the deposits are determined by comparing the filter paper containing the deposits to a set of reference filter papers.

To determine the effectiveness of the compositions of this invention as fuel stabilizers, additive mixtures comprising the methyl-imine of Primene 8I-R (Imine); a Mannich base, e.g. N-(2,6-dialkyl-4-hydroxybenzyl)-hexahydropoyrimidine or N,N-bis(2,6-dialkyl-4-hydroxybenzyl)hexahydropoyrimidine, or mixtures thereof; N,N-disalicylidene-1,2-propylenediamine (MDA); and 1,3-dicyclohexyl-5-(N,N-dimethyl-3'-aminopropyl)hexahydrotriazine (HHT) in the amounts indicated in columns 2, 3, 4, and 5 of the ensuing tables are added to fuels from various sources. These fuel mixtures are then subjected to the ASTM D-4625 storage stability test and the accelerated storage stability test as described above. Fuels which are already quite stable as determined by the foregoing stability tests, benefit less from the addition of additives than fuels which are less stable.

EXAMPLE 12

Fuel compositions of Table 1 utilize a base fuel which was obtained from Pennsylvania Crude. The stability of the fuel containing only a metal deactivator (MDA) is illustrated by Samples 1-4. Samples 5-8 of Table 1, illustrate the long and short term stability of fuel compositions containing all four additive components (i.e. Imine, Mannich base, MDA, HHT) in combination with the base fuel.

TABLE 1

| | Fuel Additive Composition (lbs/1000 Barrels) | | | | Storage Stability Data | | | |
|---|---|---|---|---|---|---|---|---|
| | | Mannich | | | F-21-61 (149° C.) | | ASTM D-4625 (43° C.) | |
| Sample | IMINE[1] | base[2] | MDA[3] | HHT[4] | Color | Deposits | Color | Deposits (mg/100 ml) |
| 1 | 0.00 | 0.00 | 0.13 | 0.00 | 8.0 | 18.0 | <3.5 | 6.7 |
| 2 | 0.00 | 0.00 | 0.25 | 0.00 | 8.0 | 17.0 | <3.5 | 7.9 |
| 3 | 0.00 | 0.00 | 0.50 | 0.00 | <8.0 | 13.0 | 3.0 | 5.4 |
| 4 | 0.00 | 0.00 | 1.25 | 0.00 | 7.5 | 13.0 | <3.5 | 4.7 |
| 5 | 0.37 | 0.25 | 0.13 | 1.75 | <2.0 | 3.0 | 3.0 | 3.2 |
| 6 | 0.75 | 0.50 | 0.25 | 3.50 | <2.0 | 4.0 | <3.0 | 4.1 |
| 7 | 1.50 | 1.00 | 0.50 | 7.00 | <2.5 | 4.0 | 2.5 | 2.6 |
| 8 | 3.75 | 2.50 | 1.25 | 17.50 | <2.0 | 4.0 | 2.5 | 2.3 |
| 9 | 0.00 | 0.00 | 0.13 | 2.37 | 8.0 | 16.0 | <3.5 | 6.3 |
| 10 | 0.00 | 0.00 | 0.25 | 4.75 | <4.0 | 8.0 | 3.0 | 4.1 |
| 11 | 0.00 | 0.00 | 0.50 | 9.50 | <2.5 | 7.0 | <3.0 | 3.6 |
| 12 | 0.00 | 0.00 | 1.25 | 23.75 | 2.0 | 6.0 | 3.0 | 4.0 |

[1] Methyl-imine of Primene 81-R
[2] N-(2,6-dialkyl-4-hydroxybenzyl)hexahydropyrimidine or N,N-bis(2,6-dialkyl-4-hydroxybenzyl)hexahydropyrimidine
[3] N,N-disalicylidene-1,2-propylenediamine
[4] 1,3-dicyclohexyl-5-(N,N-dimethyl-3'-aminopropyl) hexahydrotriazine

EXAMPLE 13

Fuel compositions of Table 2 utilize a base fuel which was obtained from Illinois Basin Crude. The stability of the fuel containing only a metal deactivator (MDA) is illustrated by Samples 1–4. Samples 5–8 of Table 2, illustrate the long and short term stability of fuel compositions containing all four additive components (i.e. imine, Mannich base, MDA, HHT) in combination with the base fuel.

EXAMPLE 14

Fuel compositions of Table 3 utilize a base fuel which was obtained from a Midcontinent Crude. The stability of the base (unadditized) fuel is illustrated by Sample 1. Samples 2–3 of Table 3, illustrate the long and short term stability of fuel compositions containing all four additive components (i.e. Imine, Mannich base, MDA, HHT) in combination with the fuel of Sample 1.

TABLE 2

| | Fuel Additive Composition (lbs/1000 Barrels) | | | | Storage Stability Data | | | |
|---|---|---|---|---|---|---|---|---|
| | | Mannich | | | F-21-61 (149° C.) | | ASTM D-4625 (43° C.) | |
| Sample | IMINE[1] | base[2] | MDA[3] | HHT[4] | Color | Deposits | Color | Deposits (mg/100 mL) |
| 1 | 0.00 | 0.00 | 0.13 | 0.00 | <6.0 | 7.0 | <5.0 | 11.3 |
| 2 | 0.00 | 0.00 | 0.25 | 0.00 | <6.0 | 7.0 | <5.0 | 9.2 |
| 3 | 0.00 | 0.00 | 0.50 | 0.00 | 6.5 | 8.0 | <5.0 | 7.1 |
| 4 | 0.00 | 0.00 | 1.25 | 0.00 | 8.0 | 13.0 | <5.0 | 9.2 |
| 5 | 0.37 | 0.25 | 0.13 | 1.75 | <6.5 | 12.0 | <4.5 | 5.9 |
| 6 | 0.75 | 0.50 | 0.25 | 3.50 | 5.5 | 10.0 | 4.0 | 4.5 |
| 7 | 1.50 | 1.00 | 0.50 | 7.00 | <3.0 | 5.0 | <4.0 | 2.9 |
| 8 | 3.75 | 2.50 | 1.25 | 17.50 | 3.0 | 5.0 | 3.5 | 3.0 |
| 9 | 0.00 | 0.00 | .013 | 2.37 | 6.0 | 11.0 | 5.0 | 10.7 |
| 10 | 0.00 | 0.00 | 0.25 | 4.75 | <4.0 | 8.0 | <4.5 | 5.8 |
| 11 | 0.00 | 0.00 | 0.50 | 9.50 | <3.0 | 6.0 | <4.0 | 3.7 |
| 12 | 0.00 | 0.00 | 1.25 | 23.75 | <3.0 | 6.0 | <3.5 | 3.5 |

[1] Methyl-imine of Primene 81-R
[2] N,N-dimethylcyclohexylamine
[3] N,N-disalicylidene-1,2-propylenediamine
[4] 1,3-dicyclohexyl-5-(N,N-dimethyl-3'-aminopropyl) hexahydrotriazine

TABLE 3

| | Fuel Additive Composition (lbs/1000 Barrels) | | | | Storage Stability Data | | | |
|---|---|---|---|---|---|---|---|---|
| | | Mannich | | | F-21-61 (149° C.) | | ASTM D-4625 (43° C.) | |
| Sample | IMINE[1] | base[2] | MDA[3] | HHT[4] | Color | Deposits | Color | Deposits (mg/100 mL) |
| 1 | 0.00 | 0.00 | 0.00 | 0.00 | 3.5 | 3.0 | <4.5 | 3.2 |
| 2 | 0.75 | 0.50 | 0.25 | 3.50 | <3.5 | 3.0 | 4.0 | 1.7 |
| 3 | 1.50 | 1.00 | 0.50 | 7.00 | <3.0 | 4.0 | <4.0 | 1.9 |
| 4 | 0.00 | 0.00 | 0.25 | 4.75 | <3.5 | 4.0 | 4.0 | 2.1 |
| 5 | 0.00 | 0.00 | 0.50 | 9.50 | 2.5 | 4.0 | <4.0 | 1.6 |

[1] Methyl-imine of Primene 81-R
[2] N,N-dimethylcyclohexylamine
[3] N,N-disalicylidene-1,2-propylenediamine
[4] 1,3-dicyclohexyl-5-(N,N-dimethyl-3'-aminopropyl) hexahydrotriazine

EXAMPLE 15

Fuel compositions of Table 4 utilize a base fuel which was obtained from a Midcontinent Crude (typical No. 2 Diesel Fuel). The stability of the base (unadditized) fuel is illustrated by Sample 1. Samples 3–4 of Table 4, illustrate the long and short term stability of fuel compositions containing all four additive components (i.e. Imine, Mannich base, MDA, HHT) in combination with the fuel of Sample 1.

TABLE 4

| | Fuel Additive Composition (lbs/1000 Barrels) | | | | Storage Stability Data | | | |
|---|---|---|---|---|---|---|---|---|
| | | Mannich | | | F-21-61 (149° C.) | | ASTM D-4625 (43° C.) | Deposits |
| Sample | IMINE[1] | base[2] | MDA[3] | HHT[4] | Color | Deposits | Color | (mg/100 mL) |
| 1 | 0.00 | 0.00 | 0.00 | 0.00 | 5.0 | 8.0 | <5.0 | 3.5 |
| 2 | 0.00 | 0.00 | 0.15 | 0.00 | <5.0 | 8.0 | <5.0 | 3.1 |
| 3 | 0.45 | 0.30 | 0.15 | 2.10 | <4.0 | 5.0 | <4.5 | 2.1 |
| 4 | 0.90 | 0.60 | 0.30 | 4.20 | <3.0 | 5.0 | <4.0 | 1.5 |

[1] Methyl-imine of Primene 81-R
[2] N,N-dimethylcyclohexylamine
[3] N,N-disalicylidene-1,2-propylenediamine
[4] 1,3-dicyclohexyl-5-(N,N-dimethyl-3'-aminopropyl) hexahydrotriazine

EXAMPLE 16

Fuel compositions of Table 5 utilize a base fuel which was obtained from a Midcontinent Crude (Light Cycle Oil only). The stability of the base (unadditized) fuel is illustrated by Sample 1. Samples 3–4 of Table 5, illustrate the long and short term stability of fuel compositions containing all four components (i.e. Imine, Mannich base, MDA, and HHT) in combination with the fuel of Sample 1.

TABLE 5

| | Fuel Additive Composition (lbs/1000 Barrels) | | | | Storage Stability Data | | | |
|---|---|---|---|---|---|---|---|---|
| | | Mannich | | | F-21-61 (149° C.) | | ASTM D-4625 (43° C.) | Deposits |
| Sample | IMINE[1] | base[2] | MDA[3] | HHT[4] | Color | Deposits | Color | (mg/100 mL) |
| 1 | 0.00 | 0.00 | 0.00 | 0.00 | 3.0 | 2.0 | 7.0 | 5.8 |
| 2 | 0.00 | 0.00 | 0.50 | 0.00 | <3.0 | 2.0 | <7.0 | 5.2 |
| 3 | 1.50 | 1.00 | 0.50 | 7.00 | <3.0 | 3.0 | <6.0 | 3.1 |
| 4 | 3.00 | 2.00 | 1.00 | 14.00 | <3.0 | 2.0 | 5.0 | 2.7 |
| 5 | 0.00 | 0.00 | 0.50 | 9.50 | <3.0 | 2.0 | 5.5 | 3.4 |
| 6 | 0.00 | 0.00 | 1.00 | 19.00 | <3.0 | 3.0 | 5.0 | 3.1 |

[1] Methyl-imine of Primene 81-R
[2] N,N-dimethylcyclohexylamine
[3] N,N-disalicylidene-1,2-propylenediamine
[4] 1,3-dicyclohexyl-5-(N,N-dimethyl-3'-aminopropyl) hexahydrotriazine

EXAMPLE 17

Fuel compositions of Table 6 utilize a base fuel which was obtained from Illinois Basin Crude. The stability of the base (unadditized) fuel is illustrated by Sample 1. Samples 2 and 3 of Table 6, illustrate the long and short term stability of fuel compositions containing all four additive components (i.e. imine, Mannich base, MDA, HHT) in combination with the fuel of Sample 1.

TABLE 6

| | Fuel Additive Composition (lbs/1000 Barrels) | | | | Storage Stability Data | | | |
|---|---|---|---|---|---|---|---|---|
| | | Mannich | | | F-21-61 (149° C.) | | ASTM D-4625 (43° C.) | Deposits |
| Sample | IMINE[1] | base[2] | MDA[3] | HHT[4] | Color | Deposits | Color | (mg/100 mL) |
| 1 | 0.00 | 0.00 | 0.00 | 0.00 | 4.5 | 6.0 | 3.5 | 4.3 |
| 2 | 1.13 | 0.75 | 0.37 | 5.25 | <3.0 | 2.0 | 3.0 | 1.6 |
| 3 | 2.25 | 1.50 | 0.75 | 10.50 | <2.5 | 2.0 | <3.0 | 1.2 |
| 4 | 0.00 | 0.00 | 0.38 | 0.00 | 4.0 | 6.0 | 3.0 | 3.3 |

[1] Methyl-imine of Primene 81-R
[2] N,N-dimethylcyclohexylamine
[3] N,N-disalicylidene-1,2-propylenediamine
[4] 1,3-dicyclohexyl-5-(N,N-dimethyl-3'-aminopropyl) hexahydrotriazine

EXAMPLE 18

Fuel compositions of Table 7 utilize a base fuel which was obtained from Sweet Crude from Southwest and/or Central Louisiana. Samples 2–3 of Table 7, illustrate the long and short term stability of a fuel composition containing all four components (i.e. Imine, Mannich base, MDA and HHT) in combination with the base fuel.

TABLE 7

| | Fuel Additive Composition (lbs/1000 Barrels) | | | | Storage Stability Data | | | |
|---|---|---|---|---|---|---|---|---|
| | | Mannich | | | F-21-61 (149° C.) | | ASTM D-4625 (43° C.) | Deposits |
| Sample | IMINE[1] | base[2] | MDA[3] | HHT[4] | Color | Deposits | Color | (mg/100 mL) |
| 1 | 0.00 | 0.00 | 0.75 | 0.00 | 2.5 | 3.0 | <5.5 | 6.5 |
| 2 | 2.25 | 1.50 | 0.75 | 10.50 | 2.5 | 4.0 | 4.5 | 4.0 |
| 3 | 6.75 | 4.50 | 2.25 | 31.50 | <3.0 | 2.0 | <4.5 | — |
| 4 | 0.00 | 0.00 | 0.75 | 14.25 | <3.0 | 4.0 | <4.5 | 3.8 |
| 5 | 0.00 | 0.00 | 2.25 | 42.75 | <3.0 | 3.0 | <4.5 | — |

[1] Methyl-imine of Primene 81-R
[2] N,N-dimethylcyclohexylamine
[3] N,N-disalicylidene-1,2-propylenediamine
[4] 1,3-dicyclohexyl-5-(N,N-dimethyl-3'-aminopropyl) hexahydrotriazine Variations in the invention are within the spirit and scope of the ensuing claims.

What is claimed is:

1. An additive composition suitable for use in lubricants and fuel comprising a mixture of (i) one or a mixture of substituted hexahydrotriazines of the formula

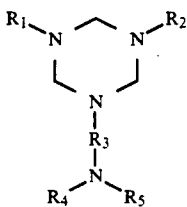

wherein $R_1$ is a hydrocarbyl group; $R_2$ is either a hydrocarbyl group or a dihydrocarbylaminoalkyl group; $R_3$ is an alkylene group having up to 12 carbon atoms; and $R_4$ and $R_5$ are hydrocarbyl groups having from 1 to 20 carbon atoms; and (ii) one or a mixture of imine compounds of the formula

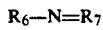

$$R_6-N=R_7$$

wherein $R_6$ is an alkyl, cycloalkyl, aryl, alkylaryl, aralkyl, having 1–40 carbon atoms, and $R_7$ is an alkyl group having 1–6 carbon atoms.

2. The additive composition of claim 1 wherein each of $R_1$ and $R_2$ is an alkyl group having from 2 to 24 carbon atoms; a cycloalkyl group having from 5 to 18 carbon atoms; or an aryl or substituted aryl group having 6 to 10 carbon atoms or a mixture thereof.

3. The additive composition of claim 2 wherein $R_4$ and are the same or different alkyl groups having from 1 to 24 carbon atoms.

4. The additive composition of claim 3 wherein $R_3$ is a propylene group.

5. The additive composition of claim 1 wherein $R_4$ and $R_5$ are the same or different alkyl groups having from 1 to 24 carbon atoms.

6. The additive composition of claim 1 wherein $R_1$ is a $C_4$ to $C_{18}$ alkyl or alkenyl group; a $C_6$ to $C_{10}$ cycloalkyl or cycloalkenyl group; or a $C_6$ to $C_{14}$ aryl group and $R_2$ is a di-($C_1$-$C_{20}$alkyl) aminopropylene group.

7. The additive composition of claim 6 wherein $R_3$ is a trimethylene group and $R_4$ and $R_5$ are methyl groups.

8. The additive composition of claim 1 wherein the hexahydrotriazine is a reaction product of cyclohexylamine, N,N-dimethyl-1,3-propane diamine, and formaldehyde.

9. The additive composition of claim 1 wherein $R_6$ is one or a mixture of tertiary alkyl groups having from 12 to 14 carbon atoms and $R_7$ is methyl.

10. The additive composition of claim 8 wherein $R_6$ is one or a mixture of tertiary alkyl groups having from 12 to 14 carbon atoms and $R_7$ is methyl.

11. A middle distillate fuel comprising minor stabilizing amount of the additive composition of claim 1.

12. A middle distillate fuel comprising a minor stabilizing amount of the additive of claim 10.

13. The middle distillate fuel of claim 12 further comprising a metal deactivator.

14. The middle distillate fuel of claim 13 wherein the metal deactivator is N,N-disalicylidene-1,2-propylene diamine.

15. The middle distillate fuel of claim 14 further comprising a Mannich base.

16. The middle distillate fuel of claim 15 wherein the Mannich base is N-(2,6-dialkyl-4-hydroxybenzyl)hexahydropyrimidine.

17. The middle distillate fuel of claim 15 wherein the Mannich base is N,N-bis(2,6-dialkyl-4-hydroxybenzyl)-hexahydropyrimidine.

18. A process for stabilizing a hydrocarbonaceous fuel comprising forming a mixture of said fuel and a stabilizing amount of (i) a hexahydrotriazine of the formula

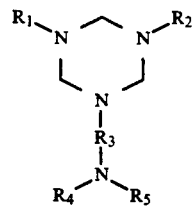

wherein $R_1$ is a hydrocarbyl group; $R_2$ is either a hydrocarbyl group or a dihydrocarbylaminoalkyl group; $R_3$ is an alkylene group having up to 12 carbon atoms; and $R_4$ and $R_5$ are hydrocarbyl groups, and (ii) an imine of the formula

$$R_6-N=R_7$$

wherein $R_6$ is an alkyl, cycloalkyl, aryl, alkylaryl, aralkyl, having 1–40 carbon atoms, and $R_7$ is an alkyl group having 1–6 carbon atoms.

19. The process of claim 18 wherein the hexahydrotriazine is the reaction product of cyclohexylamine, N,N-dimethyl-1,3-propane diamine, and formaldehyde.

20. The process of claim 19 wherein the mixture further comprises N,N-disalicylidene-1,2-propylene diamine.

21. The process of claim 20 further wherein the mixture further comprises a Mannich base.

22. The process of claim 21 wherein the Mannich base is N-(2,6-dialkyl-4-hydroxybenzyl)hexahydropyrimidine.

23. The process of claim 21 wherein the Mannich base is N,N-bis(2,6-dialkyl-4-hydroxybenzyl)hexahydropyrimidine.

24. The additive composition of claim 18 wherein $R_6$ is one or a mixture of tertiary alkyl groups having from 12 to 14 carbon atoms and $R_7$ is methyl.

25. The additive composition of claim 21 wherein $R_6$ is one or a mixture of tertiary alkyl groups having from 12 to 14 carbon atoms and $R_7$ is methyl.

26. The process of claim 25 wherein the stabilizing amount comprises from about 5 to about 95 percent by weight hexahydrotriazine and from about 95 to about 5 percent by weight imine.

27. The process of claim 18 wherein the stabilizing amount comprises from about 5 to about 95 percent by weight hexahydrotriazine and from about 95 to about 5 percent by weight imine.

* * * * *

UNITED STATES PATENT AND TRADEMARK OFFICE
CERTIFICATE OF CORRECTION

PATENT NO. : 5,162,049

DATED : November 10, 1992

INVENTOR(S) : John G. Bostick and Lawrence J. Cunningham

It is certified that error appears in the above-identified patent and that said Letters Patent is hereby corrected as shown below:

Col. 7, Line 31, change "Mannich base" to -- $DMCA^2$ --

Col. 7, Table 2, title of Column 3 therein, change "Mannich base$^2$" to -- $DMCA^2$ --

Col. 8, Line 30, change "Mannich base" to -- $DMCA^2$ --

Col. 8, Table 3, title of Column 3 therein, change "Mannich base$^2$" to -- $DMCA^2$ --

Col. 9, Line 26, change "Mannich base" to -- $DMCA^2$ --

Col. 9, Table 4, title of Column 3 therein, change "Mannich base$^2$" to -- $DMCA^2$ --

Col. 9, Line 68 to Col. 10, Line 1, change "Mannich base" to -- $DMCA^2$ --

Col. 10, Table 5, title of Column 3 therein, change "Mannich base$^2$" to -- $DMCA^2$ --

Col. 10, Line 27, change "Mannich base" to -- $DMCA^2$ --

Col. 10, Table 6, title of Column 3 therein, change "Mannich base$^2$" to -- $DMCA^2$ --

Col. 10, Lines 66-67, change "Mannich base" to -- $DMCA^2$ --

Col. 11, Table 7, title of Column 3 therein, change "Mannich base$^2$" to -- $DMCA^2$ --

Col. 14, Line 1, change "additive composition" to -- process --

UNITED STATES PATENT AND TRADEMARK OFFICE
CERTIFICATE OF CORRECTION

PATENT NO. : 5,162,049
DATED : November 10, 1992
INVENTOR(S) : John G. Bostick, et. al.

It is certified that error appears in the above-indentified patent and that said Letters Patent is hereby corrected as shown below:

Col. 14, line change "additive composition" to -- process --

Signed and Sealed this

Eleventh Day of January, 1994

Attest:

BRUCE LEHMAN

Attesting Officer

Commissioner of Patents and Trademarks